(12) United States Patent
Braune et al.

(10) Patent No.: US 8,581,002 B2
(45) Date of Patent: Nov. 12, 2013

(54) PROCESS FOR WORKING UP DIACETONE ACRYLAMIDE SOLUTIONS FOR THE PREPARATION OF PURE DIACETONE ACRYLAMIDE

(75) Inventors: Sascha Braune, Luftenberg An der Donau (AT); Bernhard Holub, Strassham (AT); Christoph Huber, Langenstein (AT)

(73) Assignee: DSM Fine Chemicals Austria NFG GmbH & Co Kg, Linz (AT)

( * ) Notice: Subject to any disclaimer, the term of this patent is extended or adjusted under 35 U.S.C. 154(b) by 395 days.

(21) Appl. No.: 12/597,960

(22) PCT Filed: May 8, 2008

(86) PCT No.: PCT/EP2008/055687
§ 371 (c)(1),
(2), (4) Date: Apr. 2, 2010

(87) PCT Pub. No.: WO2008/138856
PCT Pub. Date: Nov. 20, 2008

(65) Prior Publication Data
US 2010/0217042 A1    Aug. 26, 2010

(30) Foreign Application Priority Data

May 11, 2007    (AT) .................................. A 736/2007

(51) Int. Cl.
*C07C 231/06*    (2006.01)
(52) U.S. Cl.
USPC .......................................... 564/131; 564/130

(58) Field of Classification Search
USPC .................................................. 564/130, 131
See application file for complete search history.

(56) References Cited

FOREIGN PATENT DOCUMENTS

| JP | 10-007634 | | 1/1998 |
|---|---|---|---|
| JP | 10007634 | * | 1/1998 |

OTHER PUBLICATIONS

International Search Report for PCT/EP2008/055687, mailed Oct. 8, 2008.

* cited by examiner

*Primary Examiner* — Shailendra Kumar
(74) *Attorney, Agent, or Firm* — Nixon & Vanderhye P.C.

(57) ABSTRACT

Improved process for working up diacetone acrylamide solutions, obtained by reaction of acetone or diacetone alcohol with acrylonitrile and sulfuric acid and subsequent dilution and neutralization, in which a) the organic phase obtained subsequent to the neutralization, which comprises the crude diacetone acrylamide, is hydrolyzed by addition of an aqueous alkaline solution in order to remove acrylamide, then b) after phase separation has been carried out, the organic phase, which comprises the crude diacetone acrylamide, is neutralized by addition of an acid, and c) in succession, low-boiling-point byproducts are removed by distillation in the presence of one or more polymerization inhibitors, then t-butylacrylamide is removed by distillation and, finally, the diacetone acrylamide is isolated by product distillation, and d) the diacetone acrylamide thus obtained is converted into its final form.

7 Claims, 1 Drawing Sheet

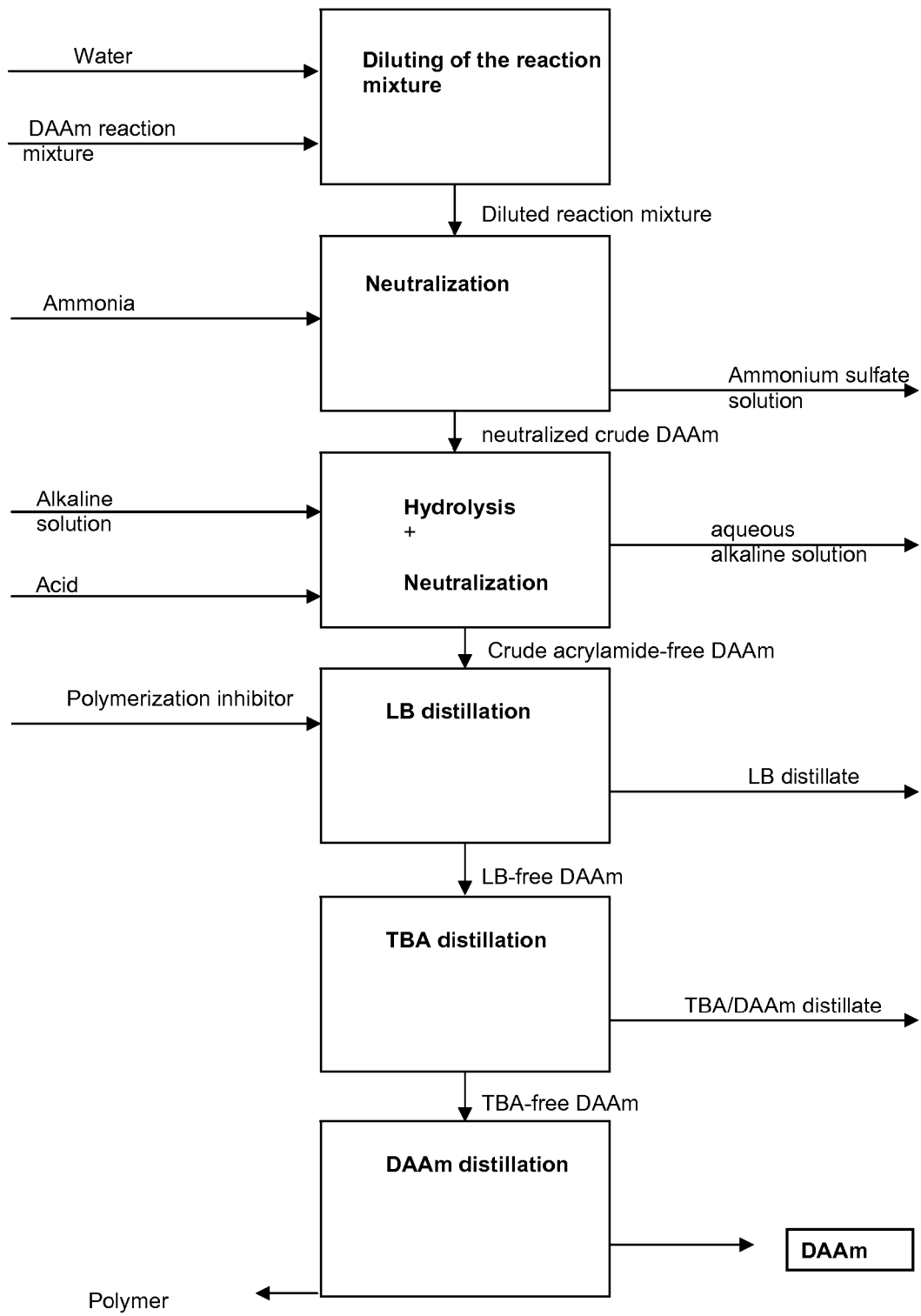

PROCESS FOR WORKING UP DIACETONE ACRYLAMIDE SOLUTIONS FOR THE PREPARATION OF PURE DIACETONE ACRYLAMIDE

This application is the U.S. national phase of International Application No. PCT/EP2008/055687 filed 8 May 2008, which designated the U.S. and claims priority to Austria Application No. A 736/2007 filed 11 May 2007, the entire contents of each of which are hereby incorporated by reference.

The present invention relates to an improved process for working up diacetone acrylamide solutions, obtained by reaction of acetone or diacetone alcohol with acrylonitrile and sulfuric acid, for the preparation of pure diacetone acrylamide without use of organic solvents.

Diacetone acrylamide (DAAm) is used as high-grade monomer for polymerization and copolymerization and is used, for example, in the manufacture of films, contact lenses, hairsprays, adhesives, dispersions and paints.

Diacetone acrylamide is prepared by the Ritter reaction of acrylonitrile with a stable, generally tertiary or secondary, carbenium ion which can be obtained by splitting off a molecular fragment, such as, for example in a dehydration, the splitting off of water, or by protonating a double bond or by a cationic rearrangement.

In the case of diacetone alcohol or acetone, the carbenium ion is generated in the presence of sulfuric acid or another suitable strong acid.

A series of byproducts, in addition, if appropriate, to unreacted starting materials, such as acrylonitrile and diacetone alcohol (DiAOH), have to be removed from the reaction mixture in the working up of the reaction solution obtained since they have various disadvantageous effects on the DAAm prepared or in the use thereof.

The following compounds may be formed as byproducts: acrylamide, a carcinogenic, sensitizing and toxic compound, the content of which in the final product DAAm should be as low as possible; t-butylacrylamide (TBA), a thermally unstable polymerization-prone compound which results, inter alia when DAAm is used as polymer additive, in undesirable byproducts.

Other byproducts result in unfavorable changes in the behavior of the product in the processing. Isophorone in particular, but also phorone, mesitylene or mesityl oxide, result, e.g., in a greasy product which cannot be processed, for example on a flaking roller.

Various processes for working up DAAm solutions for the removal of all these troublesome byproducts have already been described.

JP 57-80350 proposes a process which comprises the following steps:

The reaction mixture, obtained by reaction of acetone or DiAOH with acrylonitrile and sulfuric acid, is diluted or hydrolyzed by addition of water and subsequently neutralized with aqueous ammonia at not more than 80° C. After phase separation has been carried out, the lower ammonium sulfate/water layer is removed and discarded; the upper organic constituent layer is then worked up further.

Variant 1):
 a) aqueous extraction process: extraction with water of the water-soluble constituents, such as DAAm, from the organic constituent layer and washing of the aqueous extraction layer with a water-insoluble organic solvent; subsequently, a salting-out step is carried out, then
 b) alkali treatment process: to remove acrylamide by hydrolysis at a temperature of 50 to 80° C. with an aqueous NaOH solution and subsequent neutralization, then
 c) vacuum distillation process in the presence of polymerization inhibitors and
 d) mixing the DAAm obtained in liquid form with, for example, hydroquinone monomethyl ether (HQMME) and forming of flakes, or Variant 2):
 a) the same alkali treatment process: for the removal of acrylamide by hydrolysis at a temperature of 50 to 80° C. with an aqueous NaOH solution and subsequent neutralization, then
 b) aqueous extraction process: extraction with water of the water-soluble constituents, such as DAAm, from the organic constituent layer and washing of the aqueous extraction layer with a water-insoluble organic solvent, and then steps c) and d) follow.

In this work-up process, in both variants, the "water extraction process" with use of an organic solvent for the washing is disadvantageous, as is the salting-out step subsequent thereto in variant 1.

An additional process is known from JP 2000-159736.

The reaction mixture, obtained by reaction of acetone or DiAOH with acrylonitrile and sulfuric acid, is accordingly diluted or hydrolyzed by addition of water and subsequently neutralized with aqueous ammonia at not more than 80° C. After phase separation has been carried out, the lower ammonium sulfate/water layer is removed and discarded; the upper organic constituent layer is then worked up further.
 a) To remove acetone condensates, which cannot be removed by distillation of DAAm, the organic constituent layer is extracted with an organic solvent which is insoluble in water and which does not dissolve DAAm.
 b) The low-boiling-point constituents, such as, for example, unreacted starting materials, mesityl oxide and the cyclohexane used as extractant, are then removed by distillation in the presence of polymerization inhibitors or by blowing air into the organic layer and carrying off the low-boiling-point constituents together with the air.
 c) In the next step, alkali hydrolysis is carried out under contact with a gas comprising molecular oxygen in order to remove acrylamide, followed by neutralization.
 d) Distillation is finally carried out in the presence of polymerization inhibitors.

In this process, the extraction step with use of organic solvents is disadvantageous, though, as is the mandatory blowing in of air needed in the alkali hydrolysis for the removal of acrylamide.

It was accordingly an object of the present invention to find an improved process for the working up of DAAm solutions which avoids the disadvantages of the state of the art, in particular the use of organic solvents, and produces DAAm of high purity, not only acrylamide but also TBA and additional byproducts being able to be removed in a simple way from the DAAm and the DAAm obtained being able to be converted without any problem and in a simple way into the desired final form, for example into flakes.

A subject-matter of the present invention is accordingly an improved process for working up diacetone acrylamide solutions, obtained by reaction of acetone or diacetone alcohol with acrylonitrile and sulfuric acid and subsequent dilution and neutralization, which is characterized in that
 a) the organic phase obtained subsequent to the neutralization, which comprises the crude diacetone acrylamide, is hydrolyzed by addition of an aqueous alkaline solution in order to remove acrylamide, then b) after phase separation has been carried out, the organic phase, which comprises the crude diacetone acrylamide, is neutralized by addition of an acid, and c) in succession, first low-boiling-point byproducts are removed by distillation in the presence of one or more polymerization inhibitors, then t-butylacrylamide is removed by distillation and, finally, the diacetone acrylamide is isolated by product distillation, and d) the diacetone acrylamide thus obtained is converted into its final form. The process according to the invention is suitable for working up DAAm-comprising reaction solutions obtained by reaction of acetone or diacetone alcohol with acrylonitrile and sulfuric acid according to the state of the art.

The working-up according to the invention is represented, for example, by the flow diagram in FIG. 1.

The DAAm-comprising reaction solution obtained by reaction of acetone or diacetone alcohol with acrylonitrile and sulfuric acid is first diluted with water, analogously to the state of the art.

Subsequently, likewise analogously to the state of the art, neutralization is carried out by addition of aqueous ammonia, for example of 25% aqueous ammonia.

In this connection, as much aqueous ammonia is added to adjust a pH value from 2 to 10, preferably from 3 to 8, particularly preferably from 5 to 7. The reaction temperature should in this step be below 80° C. The reaction temperature is preferably below 70° C., particularly preferably below 60° C.

In this connection, the reaction mixture is preferably stirred. After neutralization has been carried out, further stirring is optionally carried out for some time yet, for example up to 2 h, and phase separation is subsequently initiated by leaving to stand at ambient temperature.

After phase separation has been carried out, the lower layer, comprising ammonium sulfate, is removed. This layer can, for example, be recovered in value by recrystallizing ammonium sulfate, removing it and using it as additive for fertilizers.

The upper organic layer, which comprises the crude neutralized DAAm, is then further purified.

First, acrylamide is removed by means of hydrolysis. For this, the organic layer is treated with an alkaline solution. Aqueous NaOH, KOH, LiOH or $NH_3$ or mixtures thereof, for example, are suitable as alkaline solution. Use is preferably made of NaOH and KOH or a mixture thereof, particularly preferably NaOH. The reaction temperature is 50 to 90° C., preferably 55 to 65° C., for this step.

In this connection, the alkaline solution is added, based on the acrylamide present in the organic phase, in an amount of 2 to 10 equivalents, preferably of 3 to 7 equivalents, in the form of a 5 to 50% by weight, preferably 15 to 25% by weight, aqueous solution.

After hydrolysis has been carried out, the reaction mixture is stirred further for some time yet, for example 30 min to 2 h, and phase separation is subsequently initiated by leaving to stand at ambient temperature.

The aqueous alkaline solution phase, which comprises the hydrolysis product of the acrylamide (e.g. the acrylate), is then removed and sent for waste disposal.

The acrylamide content in the organic layer is now less than 0.1% by weight.

The acrylamide-free organic phase which comprises the crude DAAm is then neutralized by addition of a suitable acid, for example sulfuric acid, so that the pH is adjusted to a value from 4 to 8, preferably from 5 to 7.

In the next step, the low-boiling-point byproducts, such as, for example, unreacted acetone, DiAOH and acrylonitrile, phorone, mesitylene, mesityl oxide and partially isophorone, are removed by distillation (low boiler distillation).

The low boiler (LB) distillation takes place in the presence of normal amounts of one or more polymerization inhibitors, such as, for example, hydroquinone, hydroquinone monomethyl ether (HQMME), phenothiazine, diphenylamine or copper powder.

A combination of phenothiazine and HQMME is preferably used.

For example, the amount of HQMME used depends on the specification desired for the DAAm final product, since HQMME virtually 100% codistills with DAAm.

The amount of phenothiazine added can be greater, since this polymerization inhibitor remains in the bottoms.

The distillation takes place under a vacuum of up to 25 mbar, preferably from 10 to 20 mbar.

The reaction temperature is at most 85° C., preferably at most 80° C.

In addition to the low boilers referred to above, water is also distilled off in this step, so that the water content of the remaining solution corresponds to the desired specification of the DAAm final product.

After removal of the LB compounds, the content of mesityl oxide is less than 1% by weight and the content of the other LB constituents (with the exception of isophorone) is less than 0.1% by weight.

The next distillation step is used for the removal of TBA and the remaining isophorone.

This distillation step is carried out at a temperature of from 80 to at most 150° C., preferably from 90 to 105° C., and a pressure of from 0.01 to 20 mbar, preferably from 1 to 5 mbar.

Suitable distillation equipment in this connection is that which makes possible a short residence time of the bottoms mixture in the equipment and accordingly a gentle distillation.

The distillation can be carried out both batchwise and continuously, the continuous operation being preferred.

It is advantageous in this connection for a number of theoretical plates=1 to be present. A number of theoretical plates from 1 to 5 is preferred.

By this step, TBA is gently depleted to a value of less than 0.4% by weight, preferably to less than 0.2% by weight, and isophorone is completely and gently removed.

Pure DAAm is then isolated from the remaining reaction solution by a product distillation, separation being achieved from compounds or polymers of DAAm with higher boiling points which may still be present.

This distillation is carried out at a temperature of from 100 to 130° C., preferably from 110 to 120° C., and a pressure of from 0.01 to 5 mbar, preferably from 0.01 to 2 mbar and particularly preferably of less than 1 mbar.

The distillation can be carried out both batchwise and continuously, the continuous operation being preferred.

The product distillation is preferably carried out in a short-path evaporator.

In the final step, the pure DAAm is converted into the desired final form by measures known from the state of the art.

For example, DAAm is converted into the flake form using a flaking roller. However, it is also possible to convert DAAm into a flowable form by compression granulating or prilling.

The DAAm thus obtained exhibits an APHA color value of at most 100.

DAAm is obtained, by the process for working up according to the invention, in high purity (TBA<0.4% by weight, preferably<0.2% by weight; acrylamide<0.1% by weight, mesityl oxide<1% by weight, LB<0.1% by weight) and a content of =98% by weight, without the addition of organic solvents, and can, for example, be put onto the market after simpler and more economical flaking.

If appropriate, it is possible, after the 1st neutralization step or after the hydrolysis and neutralization with an acid, for a further increase in the DAAm content, to carry out an extraction step with a nonpolar extractant, preferably from the group consisting of heptane, cyclohexane or petroleum ether.

Expensive solid routes are lacking in this connection and an expansion in daily output and in the campaigns is simplified or made possible.

The process is advantageous both ecologically and economically in comparison with processes for working up known hitherto.

EXAMPLE 1

A DAAm reaction solution obtained by appropriate reaction of acrylonitrile with diacetone alcohol (DiAOH) in the presence of sulfuric acid was worked up according to the invention.

The DAAm content of this solution was 29.7% by weight.
The starting content of impurities was, in this connection:
2.2% by weight of acetone, 0.2% by weight of acrylonitrile, 2.1% by weight of mesityl oxide, 0.13% by weight of DiAOH, 0.18% by weight of TBA, 0.58% by weight of mesitylene; 0.07% by weight of phorone, 0.5% by weight of isophorone; 3.6% by weight of acrylamide.

Diluting and Neutralizing 959 g of DAAm reaction solution were run dropwise with stirring over 50 minutes into 555 g of precharged water in a cooled Schmizo. The temperature rose in the process to at most 17° C. Subsequently, 718 g of ammonia (25% by weight) were further run in dropwise with stirring over 40 minutes, in order to adjust the pH to a value of 5. After stirring at 55-59° C. for 1 h and after phase separation had been carried out, 1765 g of aqueous phase, which was sent for waste disposal, and 437 g of organic phase were obtained (content of DAAm: 64.0% by weight).

Hydrolysis:

272 g of KOH (25% by weight) were added to 436 g of the organic phase and the mixture was stirred at 60° C. for 2 hours. Subsequently, phase separation was carried out at ambient temperature, whereby 320 g of aqueous phase, which was sent for waste disposal, and 381 g of organic phase (DAAm content: 67.8% by weight) were obtained.

The acrylamide content of the organic phase was 0.05% by weight.

PH Adjustment

The organic phase was adjusted to pH 5 with 6.7 g of conc. $H_2SO_4$ of pH>14.0 with stirring.

Low Boiler Distillation:

15.9 mg of HQMME and 294.0 mg of phenothiazine dissolved in 15 ml of acetone were added as stabilizing solution to 399.3 g of the organic phase.

The distillation was carried out at 85° C. in a 1000 ml Schmizo with a Claisen bridge and a membrane pump.

The pressure was reduced during the distillation from standard pressure to 30 mbar.

After 1 h 20 minutes, 305.9 g of the distillation bottomss with a DAAM content of 81.5% by weight were obtained.

TBA Distillation:

305.9 g of reaction mixture, obtained from the low boiler distillation, were distilled in a distillation apparatus with a separation stage at a temperature of from 100 to 103° C. The pressure during the distillation was from 0.1 to 0.5 mbar.

After 3 h 30 minutes, 270.3 g of distillation bottomss with a DAAm content of 83.6% by weight were obtained. The TBA content was 0.3% by weight.

DAAM Product Distillation:

Finally, a product distillation in a short-path evaporator (SPE) was carried out with a separation stage at 120° C., use being made of 270.3 g of reaction solution obtained from the TBA distillation.

The pressure during the distillation was from 0.01 to 0.5 mbar.

After 2 h 50 minutes, 206.9 g of yellowish distillate with a DAAm content of approximately 97.9% by weight were obtained. The acrylamide, TBA and water contents of the product were 0.03% by weight (acrylamide), 0.13% by weight (TBA) and <0.4% by weight (water).

Overall DAAm yield: 79.5% of theoretical yield.

EXAMPLE 2

The method according to Example 1 was repeated with an additional extraction step. The diluting, neutralizing, hydrolysis and pH adjustment steps were carried out analogously to Example 1.

Use was made of 1103 g of DAAm reaction solution with a DAAm content of 29.6% by weight.

The starting content of impurities was, in this connection:
1.4% by weight of acetone, 0.2% by weight of acrylonitrile, 2.5% by weight of mesityl oxide, 0.13% by weight of DiAOH, 0.64% by weight of TBA, 0.57% by weight of mesitylene; 0.16% by weight of phorone; 0.25% by weight of isophorone; 3.8% by weight of acrylamide.

Subsequent to the pH adjustment, an extraction was carried out with heptane. For this, 427 g of the organic phase were diluted with 158 g of water and subsequently extracted with 413 g of n-heptane. After phase separation had been carried out, 536 g of the organic phase were then extracted with 412 g of n-heptane, whereupon, in turn, after phase separation had been carried out, 557 g of organic phase were obtained, which were then further worked up analogously to Example 1 (LB distillation, TBA distillation and product distillation).

229.7 g of yellowish distillate with a DAAm content of 98.5% by weight were obtained.

The contents of impurities in the product were 0.03% by weight of acrylamide, 0.18% by weight of TBA and <0.4% by weight of water.

Overall DAAm yield: 69% of the theoretical yield.

The invention claimed is:

1. An improved process for working up of a diacetone acrylamide solution obtained by reaction of acetone or diacetone alcohol with acrylonitrile and sulfuric acid and subsequent dilution and neutralization, wherein the process comprises:
   a) hydrolyzing an organic phase which comprises crude diacetone acrylamide obtained subsequent to the neutralization of the diacetone acrylamide solution by addition of an aqueous alkaline solution in order to remove acrylamide, then subsequently
   b) after phase separation has been carried out, neutralizing the organic phase which comprises the crude diacetone acrylamide by addition of an acid, then
   c) in succession, c1) removing, by distillation in the presence of one or more polymerization initiators, low-boiling-point byproducts then c2) removing t-butylacrylamide by distillation carried out at a temperature of from 80 to 150° C. and a pressure of from 0.01 to 20 mbar, and, finally, c3) isolating the diacetone acrylamide by product distillation carried out at a temperature of from 100 to 130° C. and a pressure of from 0.01 to 5 mbar, and d) converting the diacetone acrylamide thus obtained in step c) into a final form.

2. The process according to claim 1, wherein the hydrolysis of step a) is carried out by addition of a 5 to 50% by weight aqueous NaOH or KOH solution or a mixture thereof at a temperature of from 50 to 90° C.

3. The process according to claim 1, wherein step b) is practiced by adding an amount of acid sufficient for pH to be adjusted to a value of from 4 to 8.

4. The process according to claim 1, wherein the distillation of step c1) for removing low-boiling-point byproducts is carried out at a temperature of at most 85° C. and with a vacuum of up to 25 mbar.

5. The process according to claim 1, wherein the distillation of step c1) for removing low-boiling-point byproducts is carried out in the presence of one or more polymerization inhibitors selected from the group consisting of hydroquinone, hydroquinone monomethyl ether, phenothiazine, diphenylamine and copper powder.

6. The process according to claim 1, wherein the distillation of step c2) for removing t-butylacrylamide is carried out using distillation equipment with a number of theoretical plates of from 1 to 5.

7. The process according to claim 1, wherein step d) is practiced by converting the diacetone acrylamide into a flake form.

* * * * *

UNITED STATES PATENT AND TRADEMARK OFFICE
CERTIFICATE OF CORRECTION

PATENT NO. : 8,581,002 B2
APPLICATION NO. : 12/597960
DATED : November 12, 2013
INVENTOR(S) : Sascha Braune, Bernhard Holub and Christoph Huber It is certified that error appears in the above-identified patent and that said Letters Patent is hereby corrected as shown below:

In the Specification:

Column 5, line 66, delete "bottomss" and insert --bottoms--

In the Claims:

Claim 1 at column 6, line 67, delete "initiators" and insert --inhibitors--

Signed and Sealed this
Eighth Day of March, 2016

Michelle K. Lee
*Director of the United States Patent and Trademark Office*